(12) United States Patent
Tsai et al.

(10) Patent No.: US 7,067,715 B2
(45) Date of Patent: Jun. 27, 2006

(54) COMBINATIONAL USAGE OF INSULATORS AND COAT COLOR MARKER FOR HIGH EFFICIENCY TRANSGENE EXPRESSION AND VISUAL GENOTYPING IN MICE

(75) Inventors: Ting-Fen Tsai, Taipei (TW); Yi-Chun Hsiao, His-Chih (TW); Hsiao-Hui Chang, His-Chih (TW)

(73) Assignee: Level Biotechnology Inc., Taipei Hsien (TW)

( * ) Notice: Subject to any disclaimer, the term of this patent is extended or adjusted under 35 U.S.C. 154(b) by 0 days.

(21) Appl. No.: 10/700,158

(22) Filed: Nov. 3, 2003

(65) Prior Publication Data

US 2004/0175728 A1  Sep. 9, 2004

Related U.S. Application Data

(60) Provisional application No. 60/423,677, filed on Nov. 4, 2002.

(51) Int. Cl.
*C12N 15/00* (2006.01)
*C12N 15/09* (2006.01)
*C12N 15/63* (2006.01)

(52) U.S. Cl. ..................... 800/25; 435/320.1
(58) Field of Classification Search .................... 800/8, 800/13, 14, 18, 21, 25; 435/320.1
See application file for complete search history.

(56) References Cited

OTHER PUBLICATIONS

Niemann H "Transgenic farm animals get off the ground." Transgenic Research 7:73-75, 1997.*
Kappel et al. "Regulation gene expression in transgenic animals." Current Opinion in Biotechnology 3:548-553, 1992.*
Sigmund CD "Viewponit: are studies in genetically altered mice out of control?" Arterioscler Thromb Vasc Biol 20:1425-1429, 2000.*
Cameron ER "Recent advances in transgenic technology" Molecular Biotechnology 7:253-265, 1997.*
Wall RJ "New gene transfer methods." Theriogenology 57:189-201, 2002.*
Mullins et al, "Transgenesis in nonmurine species." Hypertension 22:630-633, 1993.*
Wang et al. "Isolation, cloning and sequencing of porcine agouti exon 2 (PorAex2)." Pigment Cell Res 11(3):155-157, 1998.*
Manne et al. "Mechanisms for the pleiotropic effects of the agouti gene," Proc Natl Acad Sci 92:4721-4724, 1995.*
Ahearn JM, Cloning and sequence analysis of the mouse genomic locus encoding the largest subunit of RNA polymerase II, JBC, 1987, vol. 262, pp. 10695-10705.*
Scheider MR, Transgenic mouse models for studying the functions of insulin-like growth factor-binding proteins, FASEB, 2000, vol. 14, pp. 629-640.*
Gotz J, In vivo analysis of wild-type and FTPD-17 tau transgenic mice, Annal of NY Acad of Sci, 2000, vol. 920, pp. 126-133.*
A. C. Bell, "The Protein CTCF is Required for the Enchancer Blocking Activity of Vertebrate Insulators", Cell, vol. 98, 387-396, Aug. 6, 1999.
A. C. Bell, "Insulators and Boundaries: Versatile Regulatory Elements in the Eukaryotic Genome", Science, vol. 291, Jan. 19, 2001.
J. H. Chung et al., "Characterization of the Chicken β-globin Insulator", Proc. Natl. Acad. Sci., vol. 94, pp. 575-580, Jan. 1997.
K. Dobie et al., "Variegated Gene Expression in Mice", TIG, Apr. 1997, vol. 13, No. 4.
D. M. J. Duhl et al., "Pleiotropic Effects of the Mouse *Lethal Yellow* ($A^y$) Mutation Explained by Deletion of a Maternally Expressed Gene and the Simultaneous Production of *agouti* Fusion RNAs", Development 120, 1695-1708 (1994).
D. W. Emery, et al., "Chromatin Insulator Protects Retrovirus Vectors From Chromosomal Position Effects", Proc. Natl. Acad. Sci., Aug. 1, 2000, vol. 97 No. 16, pp. 9150-9155.

(Continued)

*Primary Examiner*—Ram R. Shukla
*Assistant Examiner*—David A. Montanari
(74) *Attorney, Agent, or Firm*—Cohen, Pontani, Lieberman & Pavane (57) ABSTRACT

A method of identifying a genotype of a transgenic mouse and reducing the variability of a transagene expression in the transgenic mouse comprises the step of introducing into a mouse (a) a transgene expression cassette, (b) a coat color expression cassette and (c) an insulator positioned at 5' or 3' end of the transgene expression cassette.

14 Claims, 8 Drawing Sheets

OTHER PUBLICATIONS

T. I. Gerasimova et al., "Chromatin Insulators and Boundaries: Effects on Transcription and Nuclear Organization", Annu. Rev. Genet. 2001, 35: 193-208.

M. J. Pikaart et al., "Loss of Transcriptional Activity of a Transgene is Accompanied by DNA Metylation and Histone Deacetylation and is Prevented by Insulators", Genes & Development 12:28553-2862.

M. N. Prioleau et al., "An Insulator Element and Condensed Chromatin Region Separate the Chicken β-globin Locus from an Independently Regulated Erythroid-Specific Folate Receptor Gene", The EMBO Journal, vol. 18, No. 14, pp. 4035-4048, 1999.

F. Recillas-Targa et al., "Positional Enhancer-Blocking Activity of the Chicken β-globin Insulator in Transiently Transfected Cells", Proc. Nat'l Acad. Sci., vol. 96, No. 25, pp. 14354-14359.

T. F. Tsai et al., "Paternal Delection from *Snrpn* to *Ube3a* in the Mouse Causes Hypotoni, Growth Retardation and Partial Lethality and Provides Evidence for a Gene Contributing to Prader-Willi Syndrome", Human Molecular Genetics, 1999, vol. 8, No. 8, 1357-1364.

T. F. Tsai, et al., "Evidence for Translational Regulation of the Imprinted *Snurgf-Snrpn* locus in Mice", Human Molecular Genetics, 2002, vol. 11, No. 14, 1659-1668.

* cited by examiner

| Name | Transgenic construct | Founder number | Color effect | Neo expression |
|---|---|---|---|---|
| A. Ag | K14-Ag | 11 | 1 | - |
| B. AgNeo | K14-Ag PolII-Neo | 7 | 1 | 1 |
| C. AgNeo-5'IN4 | HS4 HS4 HS4 HS4 K14-Ag PolII-Neo | 5 | 3 | ND |
| D. AgNeo-5'IN2 | HS4 HS4 K14-Ag PolII-Neo | 11 | 6 | 7 |
| E. AgNeo-3'IN2A | K14-Ag PolII-Neo HS4 HS4 | 9 | 4 | ND |
| F. AgNeo-3'IN2B | K14-Ag PolII-Neo HS4 HS4 | 9 | 8 | 8 |

COMBINATIONAL USAGE OF INSULATORS AND COAT COLOR MARKER FOR HIGH EFFICIENCY TRANSGENE EXPRESSION AND VISUAL GENOTYPING IN MICE

RELATED APPLICATION

The present application claims priority from the provisional application Ser. No. 60/423,677, filed Nov. 4, 2002, the content of which is hereby incorporated by reference in its entirety.

BACKGROUND OF THE INVENTION

1. Field of the Invention

The present invention relates to a novel DNA construction, wherein an insulator and a coat color reporter are introduced together into a mammalian genome to reduce the variability of a foreign gene expression in a transgenic mouse and to identify the genotype with a visible marker therein.

2. Description of the Related Art

For functional genetics analysis, the techniques of genetic modifications are often used in this field. But they're time consuming and laborious, especially in mouse system. Transgenic mouse producing by pronuclear microinjection is a system often used in genetic and clinical research, but low expression rate and labor genotyping are its disadvantages. Therefore, establishing a fast and useful system will be helpful the application of transgenic mouse in related research. PCR (polymerase chain reaction) and Southern analysis are most used in transgenic mouse genotype identification, but they're time consuming. A reporter gene within DNA construct can be a good marker to assist identification of transgenic mouse, but the variability of foreign gene expression caused by position effect is a major obstacle to hamper its development. In order to achieve the reporter system, a solution needs to be provided and applied to transgenic mouse model.

The following references provide more detailed description of the relevant art. The contents of these references are hereby incorporated by reference in their entirety.

Bell A C, West A G, Felsenfeld G. (1999) The protein CTCF is required for the enhancer blocking activity of vertebrate insulators. Cell. 98: 387–396.

Bell A C, West A G, Felsenfeld G. (2001) Insulators and boundaries: versatile regulatory elements in the eukaryotic genome. Science. 291: 447–450.

Chung J H, Whiteley M, Felsenfeld G. (1993) A 5' element of the chicken beta-globin domain serves as an insulator in human erythroid cells and protects against position effect in Drosophila. Cell 74: 505–514.

Chung J H, Bell A C, Felsenfeld G. (1997) Characterization of the chicken beta-globin insulator. Proc Natl Acad Sci U S A. 94: 575–580.

Dobie K, Mehtali M, McClenaghan M, Lathe R. (1997) Variegated gene expression in mice. Trends Genet. 13: 127–30.

Duhl, D. M., Vrieling, H., Miller, K. A., Wolff, G. L. and Barsh, G. S. (1994a) Neomorphic agouti mutations in obese yellow mice. Nat. Genet. 8: 59–65.

Duhl, D. M., Stevens, M. E., Vrieling, H., Saxon, P. J., Miller, M. W., Epstein, C. J. and Barsh, G. S. (1994b) Pleiotropic effects of the mouse lethal yellow (Ay) mutation explained by deletion of a maternally expressed gene and the simultaneous production of agouti fusion RNAs. Development, 120: 1695–1708.

Emery D W, Yannaki E, Tubb J, Stamatoyannopoulos G. (2000) A chromatin insulator protects retrovirus vectors from chromosomal position effects. Proc Natl Acad Sci U S A. 97: 9150–9155.

Gerasimova T I, Corces V G. (2001) Chromatin insulators and boundaries: effects on transcription and nuclear organization. Annu Rev Genet. 35: 193–208.

Kucera G T, Bortner D M, Rosenberg M P. (1996) Overexpression of an Agouti cDNA in the skin of transgenic mice recapitulates dominant coat color phenotypes of spontaneous mutants. Dev Biol. 173: 162–173.

Pikaart M J, Recillas-Targa F, Felsenfeld G. (1998) Loss of transcriptional activity of a transgene is accompanied by DNA methylation and histone deacetylation and is prevented by insulators. Genes Dev. 12: 2852–2862.

Prioleau M N, Nony P, Simpson M, Felsenfeld G. (1999) An insulator element and condensed chromatin region separate the chicken beta-globin locus from an independently regulated erythroid-specific folate receptor gene. EMBO J. 18: 4035–4048.

Recillas-Targa F, Bell A C, Felsenfeld G. (1999) Positional enhancer-blocking activity of the chicken beta-globin insulator in transiently transfected cells. Proc Natl Acad Sci U S A. 96: 14354–14359.

Sambrook J and Russell D W. (2001). Molecular Cloning: A Laboratory Manual. Third Edition. Cold Spring Harbor Laboratory Press, Cold Spring Harbor Laboratory, New York.

Taboit-Dameron F, Malassagne B, Viglietta C, Puissant C, Leroux-Coyau M, Chereau C, Attal J, Weill B, Houdebine L M. (1999) Association of the 5'HS4 sequence of the chicken beta-globin locus control region with human EF1 alpha gene promoter induces ubiquitous and high expression of human CD55 and CD59 cDNAs in transgenic rabbits. Transgenic Res. 8: 223–235.

Tsai T F, Jiang Y H, Bressler J, Armstrong D, Beaudet A L. (1999) Paternal deletion from Snrpn to Ube3a in the mouse causes hypotonia, growth retardation and partial lethality and provides evidence for a gene contributing to Prader-Willi syndrome. Hum Mol Genet 8:1357–1364.

Tsai T F, Chen K S, Weber J S, Justice M J, Beaudet A L. (2002) Evidence for translational regulation of the imprinted Snurf-Snrpn locus in mice. Hum Mol Genet. 11: 1659–1668.

Vassar R, Rosenberg M, Ross S, Tyner A, Fuchs E. (1989) Tissue-specific and differentiation-specific expression of a human K14 keratin gene in transgenic mice. Proc Natl Acad Sci U S A. 86:1563–1567.

Vassar R, Fuchs E. (1991) Transgenic mice provide new insights into the role of TGF-alpha during epidermal development and differentiation. Genes Dev. 5: 714–727.

Wang Y, DeMayo F J, Tsai S Y, O'Malley B W. (1997) Ligand-inducible and liver-specific target gene expression in transgenic mice. Nat Biotechnol. 15: 239–43.

Wolff, G. L., Roberts, D. W., Morrissey, R. L., Greenman, D. L., Allen, R. R., Campbell, W. L., Bergman, H., Nesnow, S. and Frith, C. H. (1987) Tumorigenic responses to lindane in mice: potentiation by a dominant mutation. Carcinogenesis 8: 1889–1897

SUMMARY OF THE INVENTION

An object of the present invention is directed to a method of identifying a genotype of a transgenic mouse and reducing the variability of a transagene expression in said transgenic mouse, comprising the steps of:

a) introducing into the genome of a mouse a vector comprising a dominant coat color marker containing an expression cassette K14-Ag, a transgene expression cassette having RNA polymerase II large subunit promoter, and a copy of chicken beta-globin HS4 insulator; and b) selecting a mouse for transgenesis by visually detecting a phenotype exhibiting coat color resulting from said expression cassette K14-Ag.

Another object of the present invention is directed to a transgenic mouse made in accordance with the above described method.

A further object of the present invention is directed to a vector for identifying a genotype of a transgenic mouse and reducing the variability of a transagene expression in said transgenic mouse, comprising a dominant coat color marker containing an expression cassette K14-Ag, a transgene expression cassette having RNA polymerase II large subunit promoter, and a copy of chicken beta-globin HS4 insulator.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings:

FIG. 1. Schematic representation of transgenic constructs. (A) Construct Ag contains the K14-Ag expression cassette with the agouti cDNA driven by the keratinocyte specific K14 promoter. (B) Construct AgNeo. The Pol II-Neo expression cassette was placed into the downstream of the Ag cassette. (C) and (D), four copies (AgNeo-5'IN4) or two copies (AgNeo-5'IN2) of the chicken beta-globin HS4 insulator were inserted into the 5' flanking of the Ag cassette. Direction of the insulator is the same as the transcriptional direction of the Ag cassette. (E) and (F), two copies of the chicken beta-globin HS4 insulators were inserted into the 3' flanking of the Pol II-Neo cassette. The insulators were placed in a direction same as, or opposite to the transcriptional direction of the Pol II-Neo cassette in the AgNeo-3'IN2A and the AgNeo-3'IN2B, respectively. Arrows indicate the directions of transcription and insulators.

FIG. 2. Coat color phenotype. (A) Construct Ag. The Ag transgenic line produced some degree of yellow pigmentation at the ventral coat. The dorsal coat color of Ag transgenic lines was barely indistinguishable from non-transgenic (+/+) C57BL/6 mice. The ventral color effect was more prominent in homozygous (Tg/Tg) transgenic compared to hemizygous (Tg/+) littermate. (B) Construct AgNeo. There was only one founder (#1) exhibited coat color phenotype out of seven founders obtained. Founder #1 displays tan color on the dorsum and yellow color on the ventral fur. (C) Construct AgNeo-5'IN4. (D) Construct AgNeo-5'IN2. 54.5% (6/11) of the founders change coat color of three phenotypes: a uniform yellow coat (founder #23), a mottled coat with varying degree of yellow hairs (founders #6, #7, #27, and #37), and a tan color on ventral fur (founder #25). Upper row is the founder and bottom row is the F1 progeny for each founder line. (E) Construct AgNeo-3'IN2A. 44.4% (4/9) of the founders exhibited coat color effects on both the dorsal and ventral fur. The founders were not bred for further analyzed since the integrated configuration of the tandem repeated DNA was expected to be similar with the AgNeo-5'IN2 construct. (F) Construct AgNeo-3'IN2B. 88.9% (8/9) of the founders exhibited coat color phenotypes. Five founders (#10, #12, #22, #23, and #33) and their F1 progeny were shown. The other three founders (#4, #11 and #18) were shown in FIG. 4C.

FIG. 3. Transgenic copy number, RNA expression and coat color effect of the AgNeo-5'IN2 transgenic mice. (A) Map of the AgNeo-5'IN2 transgene presented in a tandem repeated manner. Restriction enzymes and other designations are as follows: X, XbaI; B, BamHI; HS4, chicken beta-globin HS4 insulator; Ag, agouti; Neo, neomycin expression cassette. (B) The autoradiograms show the Southern blot hybridization of F1 liver DNA digested with XbaI or BamHI and hybridized to the neomycine probe. For copy number control, calculated amount of the transgenic DNA fragment equalized to 1, 5, 10, 20, and 30 copies per diploid genome was mixed with wild type mouse genomic DNA. The relative signal intensity of the transgene versus the copy number control was determined by using PhosphorImager. The films were exposed at −80° C. for 18 hours. (C) Coat color effect and northern analysis of the agouti and neomycin transgenes for the AgNeo-5'IN2 transgenic lines #6, #7, #15, #23, #25, #27, #32, and #37. Skin-v, RNA from ventral skin tissue; skin-d, RNA from dorsal skin tissue. Photo of the ethidium bromide staining of 28S rRNA was shown as RNA loading control.

FIG. 5. The Tyr-EGFP-HS4 transgenic mice. (A) Schematic representation of the transgenic construct. Tyrosinase and EGFP cDNA were driven by the mouse tyrosinase (250 bp) promoter and mouse RNA Pol II promoter, respectively. Two copies of the chicken beta-globin insulators, 5'HS4, were placed downstream to the EGFP transgene in the opposite direction with respect to the transcriptional orientation of the EGFP. (B) Example of the transgenic founders under visual and GFsP-5 excitation light. (C) Visual genotyping of transgenic newborn by their dark colorization in the eyes. (D) Visualizing transgenic offspring on postnatal day 7 by their tan color compared with the albino wild type. (E) Visualizing transgenic offspring on postnatal day 1 under GFsP-5 light.

DETAILED DESCRIPTION OF THE PRESENTLY PREFERRED EMBODIMENTS

Transgenic mice are commonly made by microinjection of the DNA into the pronucleus of fertilized eggs. The exogenous introduced DNA usually forms tandem repeats of 5–50 copies and integrated randomly at a single site in the genome (Dobie et al., 1997). A large portion of integrated transgenes were silenced due to insertion of the transgene into transcriptionally silent heterochromatin region (Dobie et al., 1997). The position effect also leads to highly variable expression among transgenic lines of the same construct. In addition, spatial and temporal regulation of the transgene expression maybe affected when a transgene integrated close to a strong endogenous enhancer or a silencer that might be present in neighboring regions of the genome.

A number of DNA sequences have been identified as insulators against position effects. Insulators, a specialized DNA sequence elements, which flank some genes, may be responsible for providing a barrier against incursions from surrounding domains. The most important function and definition of insulators is to protect against position effects and/or to block distal enhancer activity (Bell et al., 1999; Recillas-Targa et al., 1999). A number of insulators have now been identified both in invertebrate species and in vertebrates, they include sites in the sea urchin histone H3 genes, the ribosomal RNA genes of Xenopus, the human T cells receptor-α/δlocus access to the promoter when appropriate. (Bell et al., 2001; Gerasimova et al., 2001). The first and best characterized insulator in vertebrate is the chicken β-globin HS4 insulator. The insulator lacks intrinsic enhancer or promoter activity of its own but blocks interaction of an enhancer and a promoter when it lies between them (Chung et al., 1993; Chung et al., 1997; Prioleau et al., 1999). Besides, the chicken β-globin HS4 insulator was shown to protect transgenes against position effects and function as a chromatin boundary in Drosophila (Chung et al., 1993), transformed cell lines (Pikaart et al., 1998), transgenic mice (Wang et al., 1997), and transgenic rabbits (Attal et al., 1999) as well as the integrated retrovirus vectors for gene therapy (Emery et al., 2000).

Laborious molecular genotyping of transgenic mice is another issue for breeding and maintenance of mouse lines. Our goal is to develop a visual genotyping system with a dominant coat color marker, eliminate labor-intensive, time-consuming, and sometimes error associated molecular process, so that transgenic genotypes are readily identified by their skin pigmentation and hair color by 7–10 days of age. In this study, we investigated the ability of the chicken β-globin HS4 insulator, in terms of copy number and orientations of the insulator, to block position effects on expression of the integrated transgenes. We also applied the dominant agouti coat color marker for visual genotyping. Expression of the agouti marker can also serve as an indicator of active chromatin region for expression of the linked transgene cassette. For these purposes, we inserted the chicken β-globin HS4 insulator into either the 5' or 3' flanking sides of the dominant coat color and a linked expression cassette. Since the transgenic DNA fragments usually inserted into a single site of the genome in a tandem repeated manner, we expected that the integrated transgenes will be surrounded with the insulators at both ends after integration. Our data demonstrated that the insulator is capable of protecting the coat color reporter and a linked transgene of interest against position effects to varying degree. With the introduction of two copies of the insulators, efficiency of transgenic expression was achieved to about 90% in one orientation of the insulator construction. These results demonstrate the feasibility of combinational usage of a dominant coat color reporter and insulators for achieving visual genotyping and efficient expression of transgene in mice.

In this invention, we investigated the ability of the combinations of insulator, in terms of copy number and orientations, to block position effects on expression of the integrated transgenes. We also applied the dominant coat color marker for visual genotyping. Expression of the coat color marker can also serve as an indicator of active chromatin region for expression of the linked transgene cassette. For these purposes of invention, insulators are inserted into either the 5' or 3' flanking sides of the dominant coat color and a linked expression cassette. Since the transgenic DNA fragments usually inserted into a single site of the genome in a tandem repeated manner, we expected that the integrated transgenes will be surrounded with the insulators at both ends after integration. This invention demonstrated that the insulator is capable of protecting the coat color reporter and a linked transgene of interest against position effects to varying degree. With the introduction of two copies of the insulators, efficiency of transgenic expression was achieved to about 90% in one orientation of the insulator construction. This invention provides the feasibility of combinational usage of a dominant coat color reporter and insulators for achieving visual genotyping and efficient expression of transgene in mice.

All references cited in the above description are incorporated by reference in their entirety.

The examples which follow are set forth to illustrate the present invention, and are not to be constructed as limiting thereof.

EXAMPLE 1

Generation of Mice with Agouti Transgene and Insulators

1. Plasmid Constructions and Transgenic Mouse Generation

Figure 1:
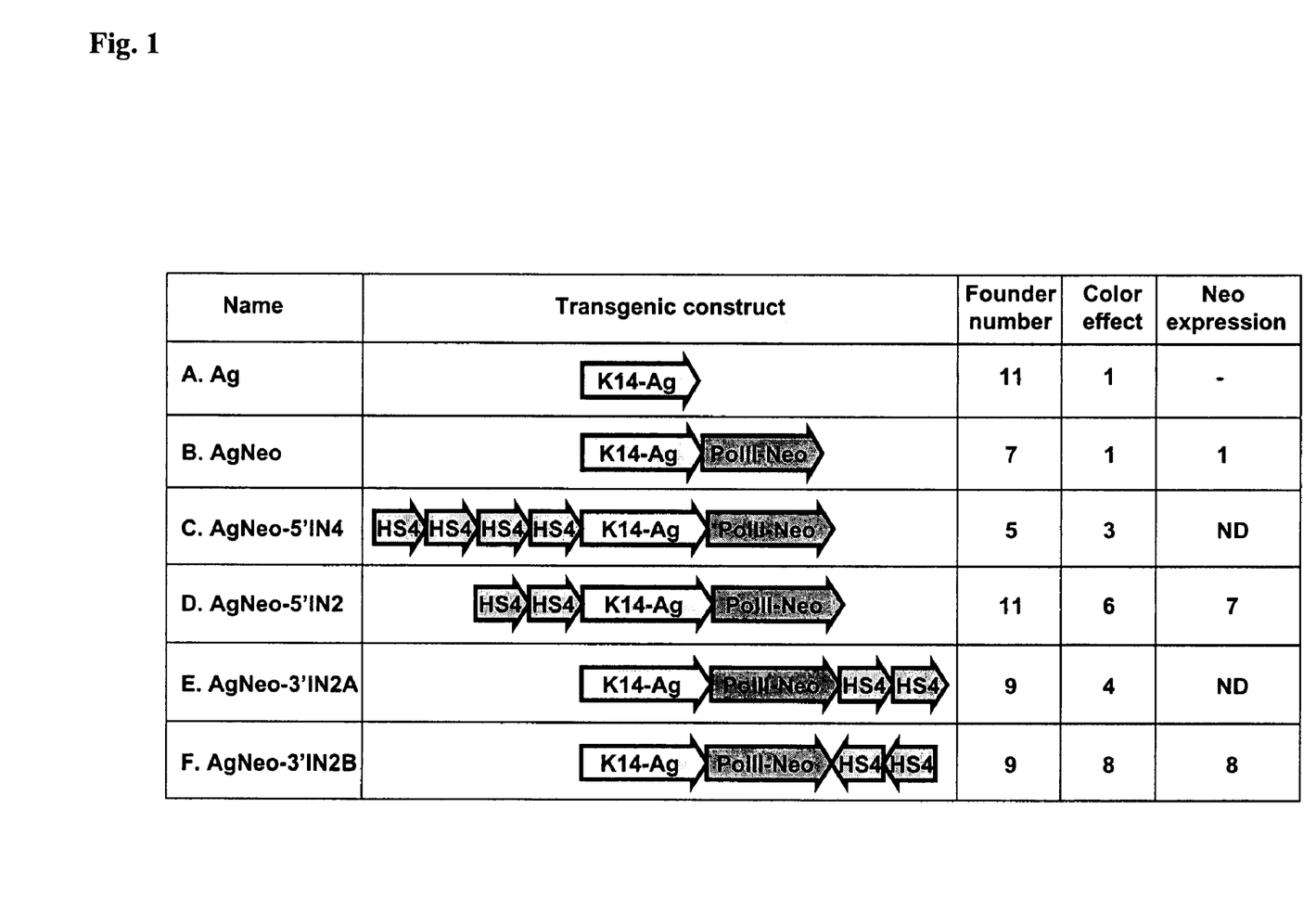

Two distinct expression cassettes were applied in these studies: (1) a dominant coat color expression cassette K14-Ag, the agouti cDNA was driven by the K14 promoter which directs keratinocyte specific expression in the skin (Vassar et al., 1989, 1991). Previous studies indicated that the pleiotropic effects associated with ectopic expression of spontaneous agouti mutations, e.g. obesity, hyperinsulinemia and hyperglycemia, were not observed when agouti was specifically expressed in the skin (Kucera et al., 1996). The agouti expression cassette thus can be used as a coat color marker in conjunction with a transgene that are targeted to express in tissues other than the skin. (2) A neomycin expression cassette Pol II-Neo, the neomycin resistant gene was expressed from the RNA polymerase II large subunit promoter. The Pol II-Neo expression cassette was designed to serve as a linked transgene of the K14-Ag cassette for evaluating co-expression efficiency of the coat color marker and the accompany transgene after integration into the mouse genome. Constructs Ag (containing K14-Ag cassette only) and AgNeo (containing K14-Ag and Pol II-Neo cassettes) are two control vectors without insulator (FIG. 1). In order to prevent positional effects on gene silencing and to optimize insulating effect, insulator with different copies number and orientations was studied. As shown in FIG. 1, we introduced a 1.2-kb DNA fragment containing the chicken beta-globin HS4 insulator into the transgenic constructs. Four and two copies of tandem repeated HS4 insulators were inserted into the 5' of the K14-Ag cassette, with the same orientation of the K14 transcription, to generate constructs AgNeo-5'IN4 and AgNeo-5'IN2, respectively (FIG. 1). In addition, two copies of the HS4 insulator were inserted into the 3' flanking of the Pol II-Neo cassette in both orientations to generate construct AgNeo-3'IN2A and AgNeo-3'IN2B. Orientation of the HS4 insulator was same as or opposite to the transcriptional direction of the Pol II-Neo cassette in the AgNeo-3'IN2A and AgNeo-3'IN2B construct, respectively (FIG. 1). We found that the insulator had no negative effects on plasmid construction and stability.

Microinjection of all these six transgenic constructs into the non-agouti (a/a) background of the C57BL/6 fertilized eggs resulted in multiple transgenic founders of each construct (FIG. 1). Transgenic founders were identified with transgene specific PCR analysis of tail DNA. Southern blot hybridization was applied to further confirm the genotypes of transgenic founders for each line. We did not observe obvious difference in the frequency of transgenics (ranged from 9.4% to 21.4%) compared to our normal transgenic frequency, indicating that the insulator fragments had no adverse effects on transgenic production.

2. Coat Color Phenotypes.

Figure 2A:
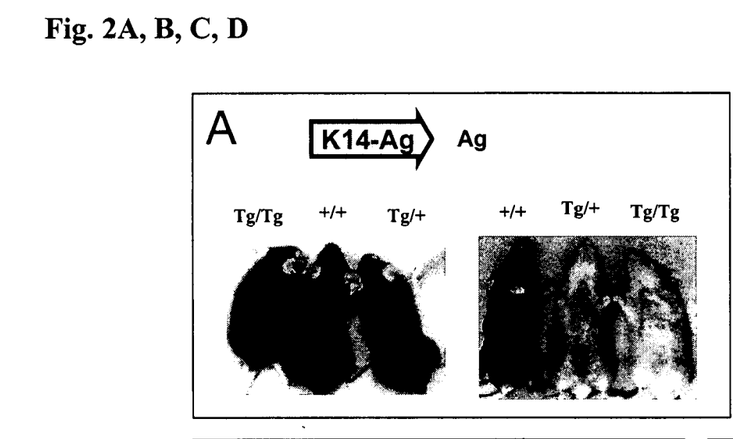

Eleven transgenic founders were obtained for the Ag construct. However, only one female founder of which had a detectable coat color phenotype on the ventral fur, and was bred with wild-type C57BL/6 male to give germ line transmission (FIG. 1). The Ag transgenic line produced some degree of yellow pigmentation at the ventral coat. The dorsal coat color of hemizygous mice was barely indistinguishable from non-transgenic C57BL6 mice (FIG. 2A). The color effect was reproducibly more prominent in mice homozygous (Tg/Tg) for the agouti transgene compared to hemizygous littermate (Tg/+) of F2 offspring (FIG. 2A). To determine whether the K14 promoter contained in our transgenic construct was sufficient to direct expression of the agouti cDNA in a tissue-specific manner, mRNA expression in multiple tissues of the Ag transgenic mice was examined by northern blot hybridization. Low level of skin-specific expression of agouti mRNA was detected in both dorsal and ventral skin (data not shown) consisting with the subtle coat phenotype of the Ag transgenic mice.

Figure 2B:
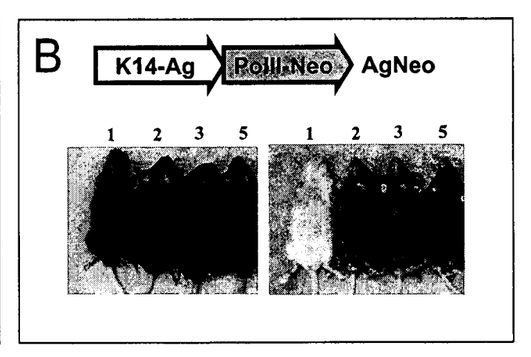

Seven transgenic founders were generated for the AgNeo construct. One out of these seven founders exhibited coat color phenotypes with tan color on the dorsum and yellow color on the ventral fur (FIG. 2B). Northern blot analysis of the neomycin mRNA of the F1 progeny exhibiting color effect indicated that the accompany Pol II-Neo transgene in the AgNeo construct was expressed (data not shown). This data indicated that the agouti coat color marker may serve as a dominant marker for both the presence and expression of the accompany transgene. The expression efficiency of the integrated transgene was 9.1% (1/11) and 14.3% (1/7) for the Ag and AgNeo transgenic mice, respectively, based on the coat color phenotype and mRNA analysis.

Figure 2C:
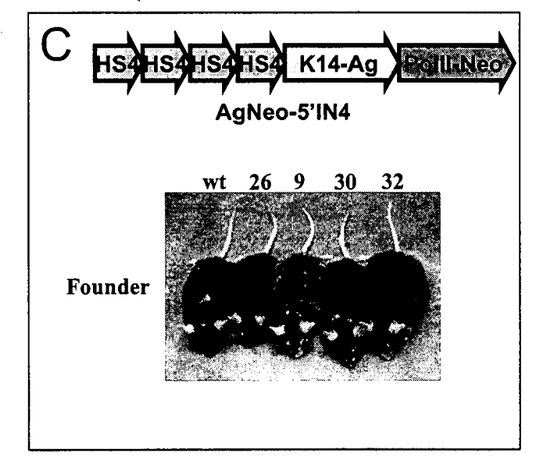
Figure 2D:
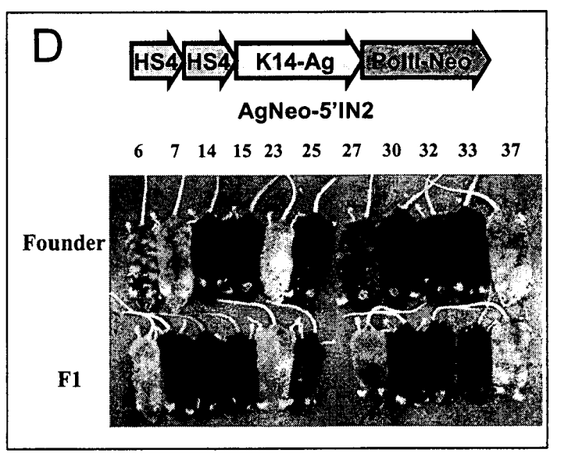

With the introduction of the insulators, efficiency of transgenic founders exhibiting coat color phenotype was greatly improved. There were 60% (3/5) and 54.5% (6/11) of the founders displayed coat color phenotypes for constructs AgNeo-5'IN4 and AgNeo-5'IN2, respectively (FIG. 1). However, four copies of insulator did not demonstrate any advantage over two copies of insulator based on the coat color phenotypes (FIGS. 2C and D). Three founders of the AgNeo-5'IN4 transgenic exhibited mottled color with small patches of yellow hairs mixed with black hairs on both dorsal and ventral fur, or only on the ventral fur (FIG. 2C). Three obvious coat color effects were observed for the AgNeo-5'IN2 transgenic lines: a uniform yellow coat (FIG. 2D, founder #23), a mottled coat with varying percentages of yellow hairs (FIG. 2D, founders #6, #7, #27, and #37), and a subtle phenotype of dark tan color (FIG. 2D, founder #25). All eleven lines of the AgNeo-5'IN2 transgenic founders were bred with C57BL/6 wild-type mice and maintained as lines to establish transmission of coat color phenotype and to correlate expression of the K14-Ag and the linked Pol II-Neo transgenes (described below). As shown in FIG. 2D and Table 1, mice with uniform yellow (founder #23), uniform black (founders #14, #15, #30, #32 and #33), and ventral tan (founder #25) coat color transmitted yellow, black, and ventral tan color, respectively, to their transgenic progeny. Founders with mottled coat color appeared to be mosaic for the presence of the transgene as they transmitted uniform coat color (FIG. 2D, yellow for F1 of lines #6, #27 and #37; dark tan for F1 of line #7) to their transgenic progeny.

Figure 2E:
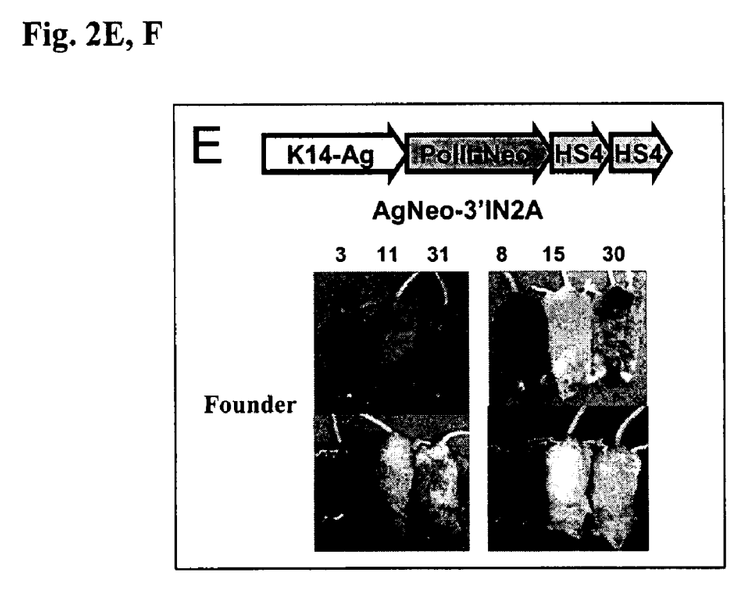

The efficiency of transgenic founders exhibiting color changes was similar for the AgNeo-3'IN2A (44.4%) and AgNeo-5'IN2 (54.5%) (FIG. 1). Coat color phenotypes for these two constructs were also similar (FIGS. 2D and E). Since the transgenic DNA fragments usually inserted into the genome in a tandem repeated manner, the integrated DNA of the AgNeo-5'IN2 and AgNeo-3'IN2A constructs will be surrounded with the insulators at both ends in the same configuration. The AgNeo-3'IN2A transgenic lines were not bred and analyzed further for mRNA expression.

Figure 2F:
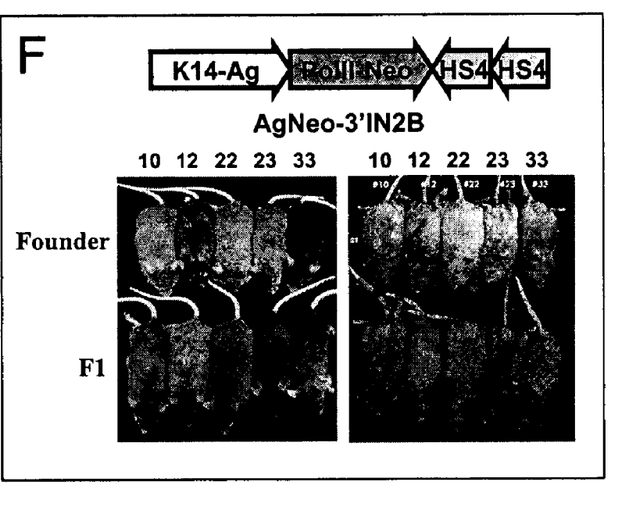

Notably, the efficiency of transgenic expression was achieved to about 90% in the AgNeo-3'IN2B transgenic lines. Obvious coat color phenotype occurred in eight transgenic lines out of a total of nine founders obtained, suggesting that the insulator protects against position effects in a way that is independent of the site of integration of the transgene (FIG. 2F and Table 2). We have tested the fertility for all of the founders obtained for the AgNeo-5'IN2 and AgNeo-3'IN2B constructs. Mice with germline transmission of the transgene were bred and maintained for molecular analysis. The transgenes were observed to been stably inherited for at least three generations, but that the coat color phenotypes often will slightly vary within lines.

3. Molecular Analysis of Transgene Expression

Figure 3A:
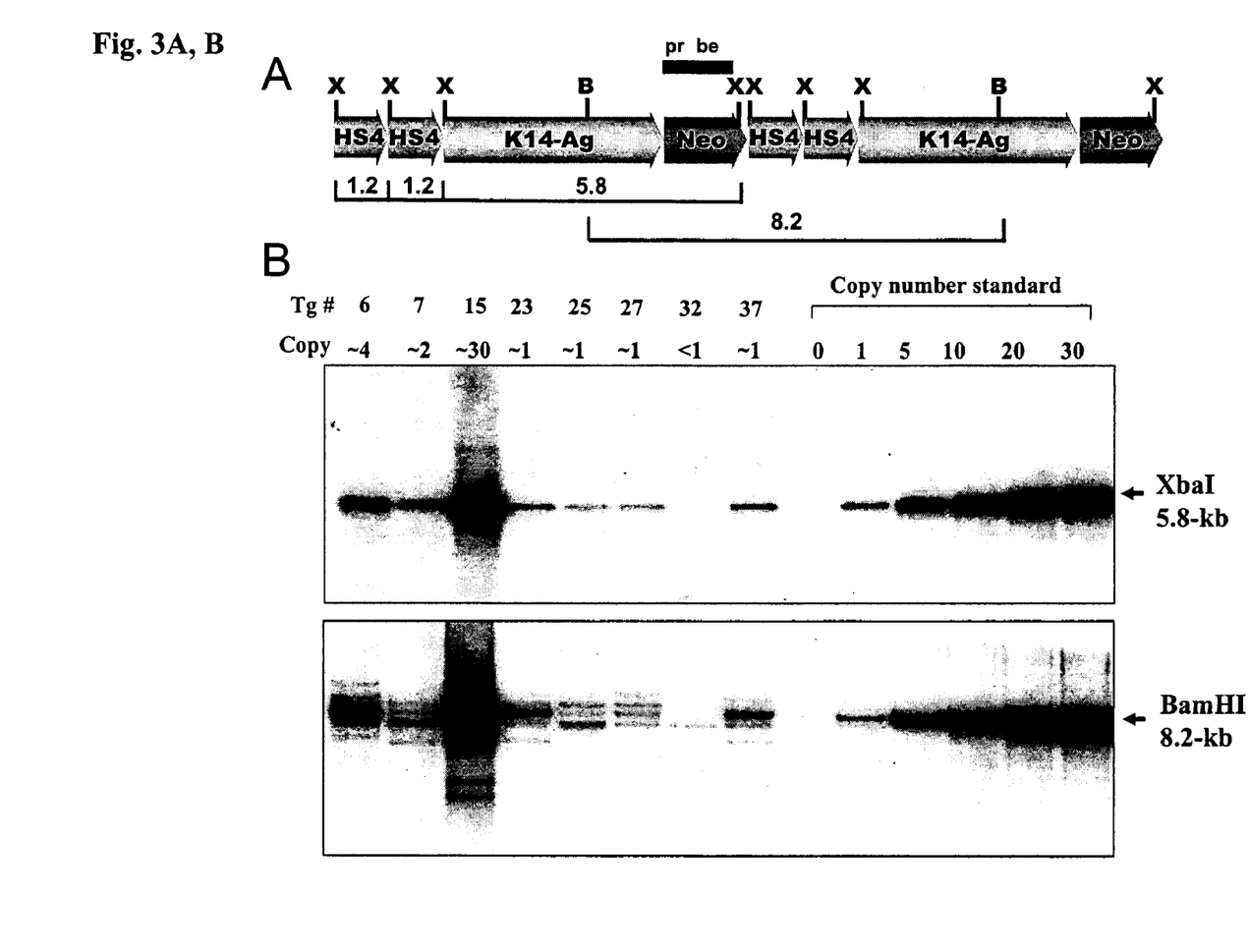
Figure 3C:
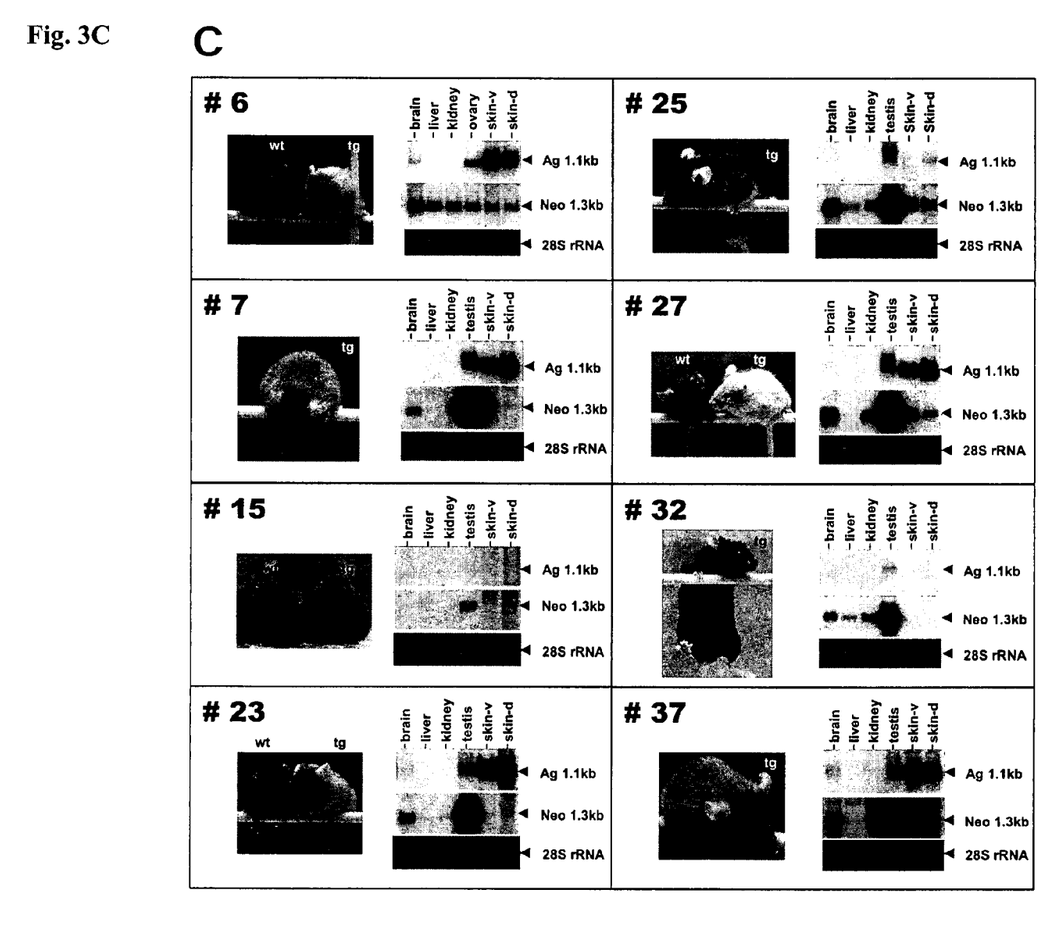
Figure 4A:
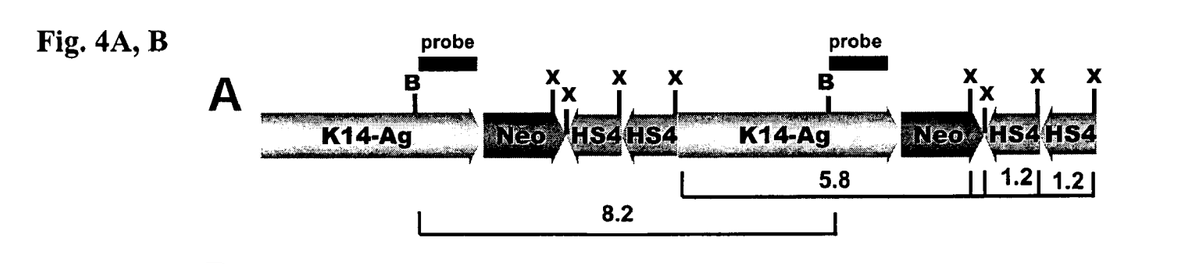
FIG. 4. Transgenic copy number, RNA expression and coat color effect of the AgNeo-3'IN2B transgenic mice. (A) Map of the AgNeo-3'IN2B transgene presented in a tandem repeated manner. (B) The autoradiograms show the Southern blot hybridization of F1 liver DNA digested with XbaI or BamHI and hybridized to the agouti cDNA probe. (C) Coat color effect and northern analysis of the agouti and neomycin transgenes for the AgNeo-3'IN2B transgenic lines #4, #10, #11, #12, #18, #22, #23, and #33. Symbols and experimental conditions are the same as described in FIG. 3.
Figure 4B:
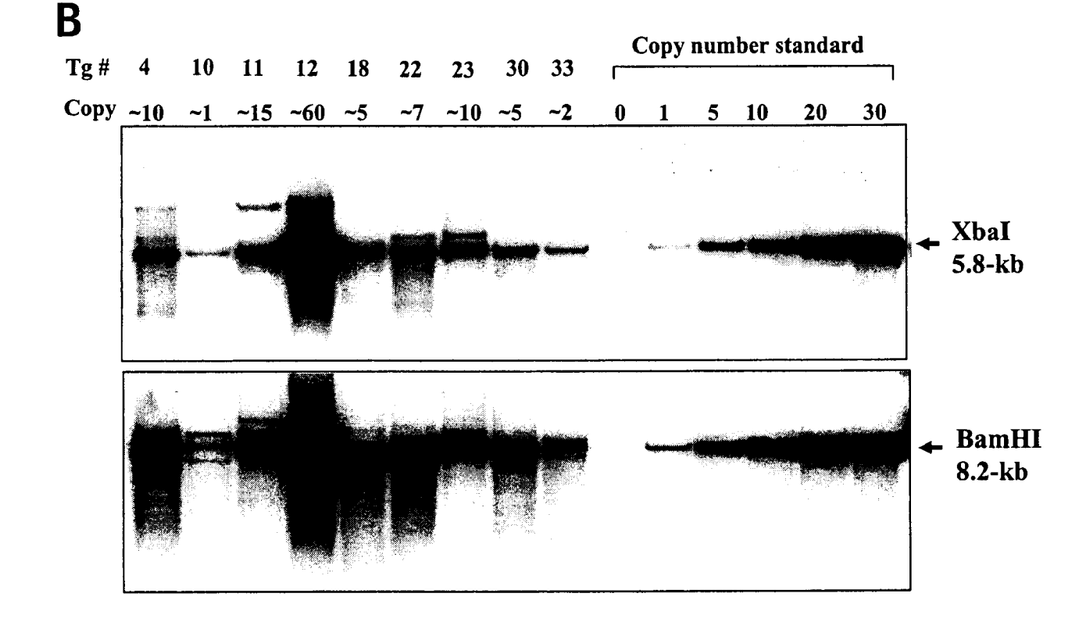

The hierarchy of coat color phenotypes in the different transgenic lines suggested that there may be a correlation between the coat color phenotype, the copy numbers of the transgene and the levels of agouti cDNA expression. As presented in FIGS. 3 and 4, Southern blot analysis of genomic DNA of the AgNeo-5'IN2 and AgNeo-3'IN2B transgenic lines demonstrated that these differences in coat color phenotypes were not simply attributable to differences in copy numbers of the agouti transgene. For example, lines #23, #25 and #32 of the AgNeo-5'IN2 transgenic mice exhibit coat color of yellow, ventral tan and black, respectively, while they all possess single copy of the agouti transgene (FIG. 3 and Table 1). Lines #10 and #12 of the AgNeo-3'IN2B transgenic mice are both phenotypically yellow, however, they possess one and 60 copies, respectively, for the transgene (FIG. 4 and Table 2). There was no correlation between coat color and copy number of the transgene.

Figure 4C:
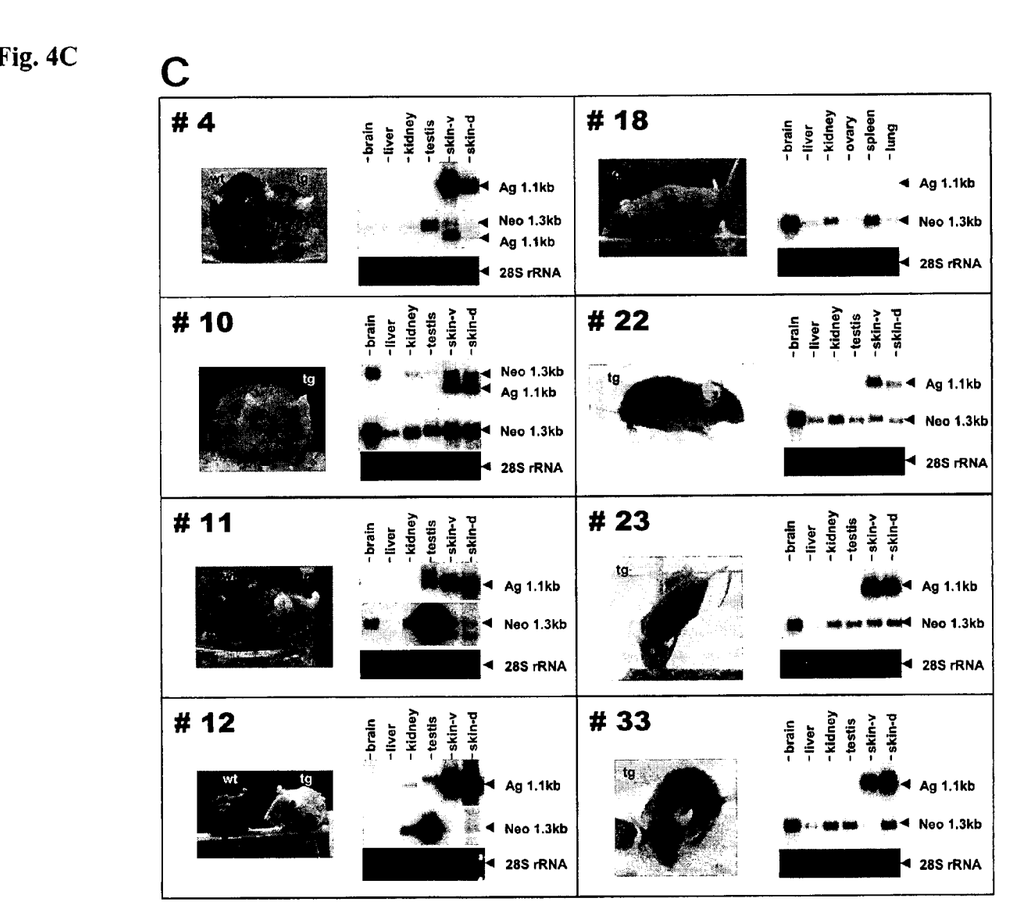

Northern blot hybridization was performed on total RNA isolated from brain, liver, kidney, testis (male), ovary (female), dorsal and ventral skin of 6–8 months old transgenic mice from different lines. As shown in FIG. 3C and FIG. 4C for the AgNeo-5'IN2 and AgNeo-3'IN2B transgenic lines, respectively, a clear correlation existed between agouti mRNA expression in the skin and the degree of phaeomelanin pigmentation observed in the coat colors. There is no detectable agouti mRNA expression in the skin of the AgNeo-5'IN2 transgenic lines #15 and #32 which exhibit black coat color (FIG. 3C). There was barely detectable agouti mRNA in the skin of the AgNeo-5'IN2 transgenic lines #25, in agree with the observation of minor color effect only on the ventral fur (FIG. 3C). Robust expression of the agouti mRNA was detectable in all of the yellow transgenic lines (FIG. 3C and FIG. 4C). Strong agouti mRNA are also detected in the mice with tan coat color (e.g. AgNeo-5'IN2 lines #7 and #37, FIG. 3C) to dark tan coat color (e.g. AgNeo-3'IN2B line #22 and #33, FIG. 4C). Low level of agouti mRNA was unexpectedly detected in the testis or ovary in most of the transgenic lines (FIG. 3C and FIG. 4C). However, our data indicated that low level of the agouti protein expressed in sex organs did not cause any overt phenotype on reproduction. All of the eleven founders of the AgNeo-5'IN2 construct and seven out of nine founders of the AgNeo-3'IN2B construct had germline transmission to their offspring (Table 1 and 2). These founders expressed the agouti mRNA in the testes or ovary from none to low level of varying degree without correlation to their fertility.

To investigate whether the coat color phenotypes can serve as a good indicator for the expression of the linked transgenic cassette, mRNA expression of the Pol II-Neo was examined by northern blot hybridization using neomycin cDNA probe. High levels of the neomycin mRNA were detected in all of the transgenic lines exhibit coat color effects (FIG. 3C and FIG. 4C). There was no correlation between strength of the coat color phenotype and levels of neomycin expression. For example, both lines #25 (ventral tan) and #27 (yellow) of the AgNeo-5'IN2 transgenic mice expressed similar levels of neomycin mRNA (FIG. 3C). For three transgenic lines without coat color changes (i.e. black), one of these three lines tested was found to express the neomycin gene (FIG. 3C, line #32). Lack of color change may due to destruction of the integrated K14-Ag gene in the AgNeo-5'IN2 #32 line based on Southern blot analysis (FIG. 3B).

EXAMPLE 2

A Coat Color Tagged Green Mouse with EGFP Expressed from the RNA Polymerase II Promoter 1. Plasmid Construction and Transgenic Generation The 712-bp HindIII-BamHI fragment containing the promoter for mouse RNA polymerase II large subunit gene (Pol II) was amplified by PCR (NCBI Accession M14101 bases 207–712). The PolII promoter was subcloned into the pBluescript II SK vector (Stratagene). The EGFP cDNA and polyA signal were isolated from pIRES-EGFP (CLONTECH) and inserted into the downstream of the Pol II promoter. Plasmid containing the chicken beta-globin HS4 insulator was kindly provided by Dr. Leo C. -K. Wang at Academia Sinica. One unit of the insulator contains 1190-bp of DNA sequence (NCBI Accession U7875 bases 10–1199). For coat color marker, the tyrosinase cDNA was amplified by RT-PCR (NCBI Accession AK014619 bases 65–1722) using skin total RNA isolated from C57 BL/6 mouse. Promoter for mouse tyrosinase (NCBI Accession D00439 from bases 2181–2544) was also generated by PCR. The intron eluted from pIRES-EGFP (CLONTECH) was inserted into the 5' of the tyrosinase cDNA. PolyA signal was from the rabbit beta-globin gene. The 6.5-kb DNA fragment was excised with NotI and SalI from plasmid Tyr-EGFP-HS4 for microinjection. DNA was microinjected into the fertilized eggs (0.5 dpc embryos) collected from the superovulated FVB/N females (Nagy et al., 2003). The injected zygotes were transferred back to the oviducts of pseudopregnant ICR foster mothers. All mice are bred and housed in specific pathogen free (SPF) facility.

2. Phenotype Analysis

Figure 5:
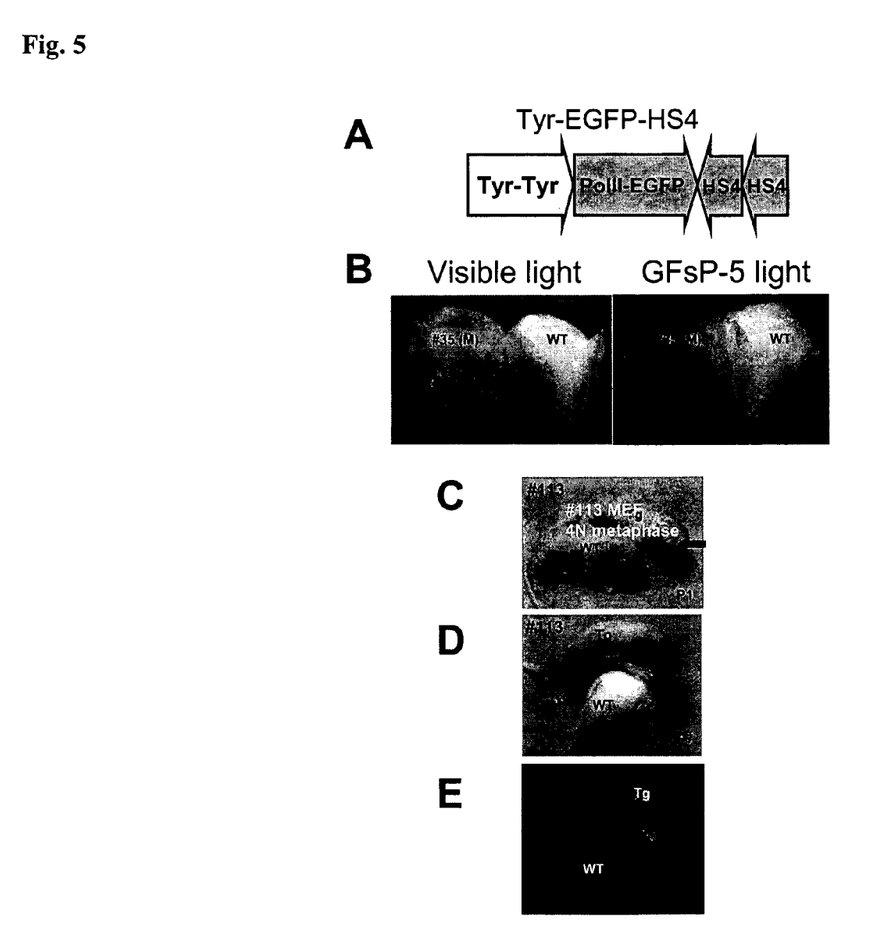

To successfully tag the EGFP gene with a visual coat color, we constructed the Tyr-EGFP-HS4 plasmid (FIG. 5A). Fourteen founders including eight males and six females were obtained. Thirteen (93%) of the founders display different degree of green fluorescence when excited with the GFsP light. Among these thirteen founders, four (29%) founders display coat color effect (lines #35, #63, #113 and #120) demonstrating a distinctly light tan coloration that was clearly different from the albino coat color (FIG. 5B). A short DNA fragment (364-bp) containing the tyrosinase promoter was applied for the transgenic study. Tight control of tissue-specific expression was observed for the 364-bp tyrosinase promoter. However, this tyrosinase promoter was relative weak when compared to the downstream RNA Pol II promoter. We found that the advantage of using this tyrosinase promoter is that whenever the founder exhibits coat color effect, the accompanying transgene was also strongly expressed (Table 3). The Tyr-EGFP-HS4 transgenic founders with light tan color (lines #35, #63, #113 and #120) were bred for germline transmission. The dark coloration on eyes of coat color-tagged transgenics offers an opportunity for visual genotyping of newborn pups right after birth on postnatal day one (FIG. 5C). The light tan color of transgenics became apparently distinguishable from albino wild type on postnatal day 7 (FIG. 5D). The newborns emitted green fluorescence with excitation light (FIG. 5E).

TABLE 1

AgNeo-5'IN2 transgenic mice

| | | Germline | Coat color | | Transgene | Neomycin | |
|---|---|---|---|---|---|---|---|
| Founder | Sex | transmission | Founder | F1 | copy | expression | %* |
| 1 #6 | F | Yes | Mottled (50% yellow) | Yellow | ~4 | Yes | 25.6 (2/7) |
| 2 #7 | F | Yes | Mottled (80% yellow) | Tan to dark tan | ~2 | Yes | 25 (3/12) |
| 3 #14 | M | Yes | Black | Black | ND | ND | ND |
| 4 #15 | M | Yes | Black | Black | ~30 | No | 62.5 (10/16) |
| 5 #23 | M | Yes | Yellow | Yellow | ~1 | Yes | 100 (8/8) |
| 6 #25 | M | Yes | Ventral tan | Ventral tan | ~1 | Yes | 25 (7/28) |
| 7 #27 | M | Yes | Mottled (30% yellow) | Yellow | ~1 | Yes | 33.3 (4/12) |
| 8 #30 | M | Yes | Black | Black | ND | ND | ND |

TABLE 1-continued

AgNeo-5'IN2 transgenic mice

| | | Germline | Coat color | | Transgene | Neomycin | |
|---|---|---|---|---|---|---|---|
| Founder | Sex | transmission | Founder | F1 | copy | expression | %* |
| 9 #32 | F | Yes | Black | Black | ~1 | Yes | 21.4 (3/14) |
| 10 #33 | M | Yes | Black | Black | ND | ND | ND |
| 11 #37 | M | Yes | Mottled (95% yellow) | Yellow to tan | ~1 | Yes | 33.3 (3/9) |

*The percentage of coat color transmission from transgenic founder to F1 offspring.

TABLE 2

AgNeo-3'IN2B transgenic mice

| | | Germline | Coat color | | Transgene | Neomycin |
|---|---|---|---|---|---|---|
| Founder | Sex | transmission | Founder | F1 | copy | expression |
| 1 #4 | M | No | Mottled (40% yellow) | ND | ~10 | Yes |
| 2 #10 | M | Yes | Yellow | Yellow | ~1 | Yes |
| 3 #11 | M | No | Mottled (50% yellow) | ND | ~15 | Yes |
| 4 #12 | M | Yes | Mottled (70% yellow) | Yellow | ~60 | Yes |
| 5 #18 | F | Yes | Mottled (80% yellow) | Yellow | ~5 | Yes |
| 6 #22 | M | Yes | Yellow | Tan | ~7 | Yes |
| 7 #23 | M | Yes | Yellow | Tan | ~10 | Yes |
| 8 #30 | F | Yes | Black | Black | ~5 | No |
| 9 #33 | M | Yes | Mottled (15% yellow) | Tan | ~2 | Yes |

TABLE 3

The Tyr-EGFP-HS4 transgenic mice.

| Founder | Sex | *Germline | Female fertility | Coat color | EGFP |
|---|---|---|---|---|---|
| 1 #35 | M | No | ND | Tan | Strong (++++) |
| 2 #63 | F | Yes | OK | Tan | Strong (+++++) |
| 3 #113 | M | Yes | OK | Tan | Strong (++++) |
| 4 #120 | M | Yes | OK | Tan | Strong (++++) |
| 5 #23 | F | ND | ND | Albino | Strong (+++++) |
| 6 #45 | F | ND | ND | Albino | Medium (+++) |
| 7 #48 | F | ND | ND | Albino | No |
| 8 #78 | M | ND | ND | Albino | Medium (++) |
| 9 #92 | M | ND | ND | Albino | Low (+) |
| 10 #93 | M | ND | ND | Albino | Medium (++) |
| 11 #106 | F | ND | ND | Albino | Medium (+++) |
| 12 #112 | M | ND | ND | Albino | Medium (+++) |
| 13 #122 | M | ND | ND | Albino | Low (+) |
| 14 #124 | F | ND | ND | Albino | Low (+) |

*Founders with tan coat color were bred for germline transmission.
M, male;
F, female;
ND, not determined.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A method of producing a transgenic mouse comprising: introducing a vector into a mouse embryo or a mouse ES cell and transferring said ES cell into a blastocyst; transferring said embryo or said blastocyst comprising said ES cell into a pseudopregnant female mouse; allowing said embryo or blastocyst to develop into an offspring; selecting an offspring that expresses agouti cDNA and has a coat color phenotype; wherein said vector comprises: a first transgene expression cassette comprising mouse agouti cDNA operably linked to a human keratinocyte specific K14 promoter, a second transgene expression cassette comprising RNA polymerase II large subunit promoter, and a chicken beta-globin HS4 insulator; wherein said insulator and said first transgene expression cassette are located at the 5' or 3' end of said second transgene expression cassette; the number of copies of said chicken beta-globin HS4 insulator is 1–6; and said insulator is in the same or opposite orientation relative to said first and second transgene expression cassettes in said vector.

2. A vector comprising a first transgene expression cassette comprising mouse agouti cDNA operably linked to a human keratinocyte specific K14 promoter, a second transgene expression cassette comprising RNA polymerase II large subunit promoter, and a chicken beta-globin HS4 insulator; wherein said insulator and said first transgene expression cassette are located at the 5' or 3' end of said second transgene expression cassette; the number of copies of said chicken beta-globin HS4 insulator is 1–6 and said insulator is in the same or opposite orientation relative to said first and second transgene expression cassettes in said vector.

3. A method of producing a transgenic mouse comprising: introducing a vector into a mouse embryo or a mouse ES cell and transferring said ES cell into a blastocyst; transferring said embryo or said blastocyst comprising said ES cell into a pseudopregnant female mouse; allowing said embryo or blastocyst to develop into an offspring; selecting an offspring that expresses agouti cDNA and has a coat color phenotype; wherein said vector comprises: a first transgene expression cassette comprising mouse agouti cDNA operably linked to a promoter, a second transgene expression cassette comprising RNA polymerase II large subunit promoter, and a chicken beta-globin HS4 insulator.

4. The method of claim 3 wherein said promoter is a human keratinocyte specific K14 promoter.

5. The method of claim 3 where said promoter is a mouse tyrosinase promoter.

6. The method of claim 3 wherein said insulator and said first transgene expression cassette are placed at the 5' and 3' end of said second transgene expression cassette.

7. The method of claim 3 wherein said number of copies of said chicken beta-globin HS4 insulator is 1–6.

8. The method of claim 3 wherein said insulator is in the same or opposite orientation relative to said first and second transgene expression cassettes.

9. A vector comprising a first transgene expression cassette comprising mouse agouti cDNA operably linked to a promoter, a second transgene expression cassette comprising RNA polymerase II large subunit promoter, and a chicken beta-globin HS4 insulator.

10. The vector of claim 9 wherein said promoter is a human keratinocyte specific K14 promoter.

11. The vector of claim 9 wherein said promoter is a mouse tyrosinase promoter.

12. The vector of claim 9 wherein said insulator and said first transgene expression cassette are placed at the 5' or 3' end of said second transgene expression cassette.

13. The vector of claim 9 wherein the number of copies of said chicken beta-globin HS4 insulator is 1–6.

14. The vector of claim 9 wherein said insulator is in the same or opposite orientation relative to said first and second transgene expression cassettes.

* * * * *

UNITED STATES PATENT AND TRADEMARK OFFICE
CERTIFICATE OF CORRECTION

PATENT NO. : 7,067,715 B2  
APPLICATION NO. : 10/700158  
DATED : June 27, 2006  
INVENTOR(S) : Yi-Chun Hsiao Page 1 of 1

It is certified that error appears in the above-identified patent and that said Letters Patent is hereby corrected as shown below:

On The Title page Item (73)  
Assignee: Level Biotechnology Inc., Taipei Hsien (TW) and National Yang-Ming University, Taipei (TW)

Signed and Sealed this

Eighteenth Day of March, 2008

JON W. DUDAS  
*Director of the United States Patent and Trademark Office*